United States Patent [19]

Ohno et al.

[11] 4,435,566

[45] Mar. 6, 1984

[54] THIOPYRANOPYRIMIDINE COMPOUNDS AND ACID ADDITION SALTS THEREOF

[75] Inventors: Sachio Ohno; Kiyoshi Mizukoshi; Osamu Komatsu; Hajimu Yamamoto; Yasuo Kunou, all of Aichi, Japan

[73] Assignee: Maruko Seiyaku Co., Ltd., Nagoya, Japan

[21] Appl. No.: 469,657

[22] Filed: Feb. 25, 1983

[30] Foreign Application Priority Data

Feb. 25, 1982 [JP] Japan ................................. 57-29594
Feb. 1, 1983 [JP] Japan ................................. 58-15097

[51] Int. Cl.³ ......................................... C07D 495/04
[52] U.S. Cl. ................................... 544/117; 544/80; 544/278
[58] Field of Search ........................... 544/117, 80, 278

[56] References Cited

U.S. PATENT DOCUMENTS

| 3,272,811 | 9/1966 | Ohnacker et al. ................. 544/278 |
| 3,316,257 | 4/1967 | Ohnacker et al. ................. 544/278 |
| 3,318,881 | 5/1967 | Ohnacker et al. ................. 544/117 |
| 3,318,883 | 5/1967 | Ohnacker et al. ................. 544/278 |

*Primary Examiner*—Robert W. Ramsuer
*Attorney, Agent, or Firm*—Sughrue, Mion, Zinn, Macpeak and Seas

[57] ABSTRACT

Novel thiopyranopyrimidine compounds and the pharmaceutically acceptable acid addition salts thereof having excellent hypoglycemic activity, platelet aggregation inhibitory activity, antihistamine activity and antiallergy activity useful for prevention and treatment of various disorders caused by diabetes, allergy and the like are disclosed.

9 Claims, No Drawings

THIOPYRANOPYRIMIDINE COMPOUNDS AND ACID ADDITION SALTS THEREOF

FIELD OF THE INVENTION

This invention relates to novel thiopyranopyrimidine compounds and the pharmaceutically acceptable acid addition salts thereof having excellent hypoglycemic activity (blood sugar lowering activity), platelet aggregation inhibitory activity, antihistamine activity and anti-allergy activity and, therefore, are useful for prevention and treatment of various disorders caused by diabetes, allergy and the like.

BACKGROUND OF THE INVENTION

Hitherto, various studies have been made on pharmacological activities of thienopyrimidine compounds as disclosed in, for examle, U.S. Pat. Nos. 3,272,811, 3,318,881 and 3,318,883, and British Pat. No. 1,048,986, etc. However, the pharmacology of thiopyranopyrimidine compound has not been studied extensively in the art.

As a result of studies on the synthesis and the utility of novel thiopyranopyrimidine derivatives, the present inventors found that the thiopyranopyrimidine compounds represented by the formula (I) and the pharmaceutically acceptable acid addition salts thereof exhibit excellent hypoglycemic activity, platelet aggregation inhibitory activity, anti-histamine and anti-allergy activity.

DETAILED DESCRIPTION OF THE INVENTION

The thiopyranopyrimidine compounds of the present invention are represented by the formula (I)

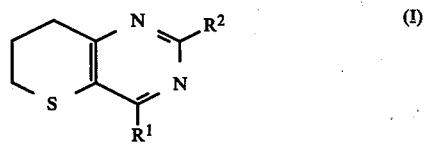

wherein $R^1$ represents an amino group, a methylamino group, a hydroxyethylamino group, a pyrrolidino group, a morpholino group, a piperazino group or an N-substituted piperazino group, and $R^2$ represents an amino group, a methylamino group, a dimethylamino group, a piperazino group, an N-substituted piperazino group, a pyrrolidino group, a piperidino group or a morpholino group, and the pharmaceutically acceptable acid addition salts thereof.

Examples of the N-substituted piperazino group of $R^1$ and $R^2$ include an N-alkylpiperazino group having 1 to 4 carbon atoms in the alkyl moiety thereof, an N-benzylpiperazino group, an N-formylpiperazino group, an N-(halobenzyl)piperazino group wherein the halogen atom is chlorine or bromine.

The pharmaceutically acceptable acid addition salts of the compounds of the formula (I) include non-toxic inorganic or organic acid salts. Preferred examples of the salts are hydrochloride, sulfate, hydrobromide, methanesulfonate, maleate, fumarate, tartrate and the like. It is to be noted that the compounds of the formula (I) can be monobasic or dibasic compounds and hence the acid addition salts thereof can be mono-acid salts or di-acid salts.

The compounds of the formula (I) of the present invention can be prepared by the following alternative procedures.

The compounds of the formula (I) wherein $R^2$ represents an amino group ($-NH_2$) can be prepared by reacting a novel starting material, 2-amino-4-chloro-7,8-dihydro-6H-thiopyrano[3,2-d]pyrimidine, represented by the formula (II)

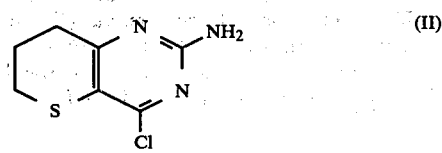

with a molar excess amount (e.g., 2 to 10 mols) of an amine ($R^1H$) which corresponds to the amine group of $R^1$, for example, ammonia, methylamine, ethanolamine, pyrrolidine, morpholine, piperazine or an N-substituted piperazine, in the absence or presence of an inert organic solvent such as dichloromethane, chloroform, benzene, methanol, ethanol, tetrahydrofuran, etc., at a temperature of about 0° to about 100° C. for a period of about 30 minutes to about 10 hours. The product thus-obtained can be preferably purified by chemical procedures well known in the art, for example, recrystallization or column chromatography, to obtain a purified product (I).

Alternatively, the compounds of the formula (I) wherein $R^2$ is an amino group ($-NH_2$) and $R^1$ is an N-substituted piperazino group can be prepared by reacting the corresponding piperazino ($R^1$) compound, 2-amino-4-piperazino-7,8-dihydro-6H-thiopyrano[3,2-d]pyrimidine, obtained as described above with an alkyl halide such as methyl bromide, ethyl bromide, propyl chloride and the like (alkylation), a benzyl halide such as benzyl chloride (benzylation) or a halobenzyl halide such as chlorobenzyl chloride, bromobenzyl chloride, fluorobenzyl chloride and the like (halobenzylation), in the presence of a base such as potassium carbonate, sodium carbonate, sodium bicarbonate and the like in a solvent such as N,N-dimethylformamide, dimethyl sulfoxide, tetrahydrofuran, etc.

The novel starting compounds represented by the formula (II) can be prepared by reacting ethyl 3-oxo-tetrahydrothiopyran-2-carboxylate represented by the formula

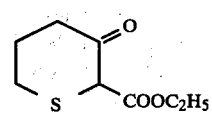

with guanidine carbonate in the presence of a base such as sodium hydroxide, potassium hydroxide, sodium methoxide, sodium ethoxide and the like, in a solvent such as methanol, ethanol, isopropyl alcohol and the like to produce a novel compound, 2-amino-4-hydroxy-7,8-dihydro-6H-thiopyrano[3,2-d]pyrimidine represented by the formula

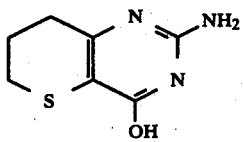

and reacting the resulting compound with phosphorus oxychloride while heating in the presence of a tertiary amine such as N,N-dimethylaniline, diethylaniline.

The compounds of the formula (I) wherein $R^2$ is a substituent other than an amino group can be prepared by reacting 2,4-dichloro-7,8-dihydro-6H-thiopyrano-[3,2-d]pyrimidine of the formula (III)

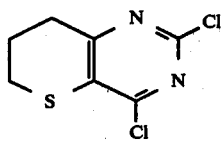

with a molar excess amount (e.g., 2 to 6 mols) of an amine ($R^1H$) which corresponds to the substituent $R^1$, for example, ammonia, methylamine, ethanolamine, morpholine, piperazine or an N-substituted piperazine, in the absence or presence of solvent such as dichloromethane, chloroform, benzene, methanol, ethanol, tetrahydrofuran, water and the like, at a temperature of about 0° to about 100° C. for a period of about 30 minutes to about 10 hours, purifying the resulting reaction product by a conventional chemical purification procedure such as recrystallization or column chromatography to obtain a novel 2-chloro-4-substituted-7,8-dihydro-6H-thiopyrano[3,2-d]pyrimidine represented by the formula (IV)

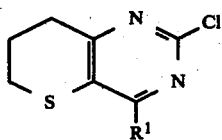

and then reacting the resulting compound (IV) with an amine ($R^2H$) which corresponds to the substituent $R^2$, for example, methylamine, dimethylamine, piperazine, an N-substituted piperazine, pyrrolidine, piperidine or morpholine under the reaction conditions as described above for the reaction between the compound (III) and the amine. The resulting product can be purified by a conventional chemical purification procedure such as recrystallization or column chromatography to obtain a purified product of the formula (I).

Alternatively, the compounds of the formula (I) wherein $R^1$ is a piperazino group can be prepared by reacting compound of the formula (III) with N-formylpiperazine to obtain 2-chloro-4-(N-formylpiperazino)-7,8-dihydro-6H-thiopyrano[3,2-d]pyrimidine, reacting the resulting compound with an amine corresponding to the substituent $R^2$ to obtain a 2-substituted-4-(N-formylpiperazino)-7,8-dihydro-6H-thiopyrano[3,2-d]pyrimidine, and de-formylating the resulting compound with a mineral acid such as hydrochloric acid, sulfuric acid and the like.

In a further alternative procedure, the compound of the formula (I) wherein $R^2$ is an N-substituted piperazino group can also be prepared from the corresponding piperadino compound in the same manner as described previously for the compound (I) wherein $R^1$ is an N-substituted piperazino group and $R^2$ is —$NH_2$, i.e., by alkylation, benzylation, halobenzylation, etc.

The starting material, 2,4-dichlorothiopyranopyrimidine, of the formula (III) is a novel compound and can be prepared by the following reaction scheme:

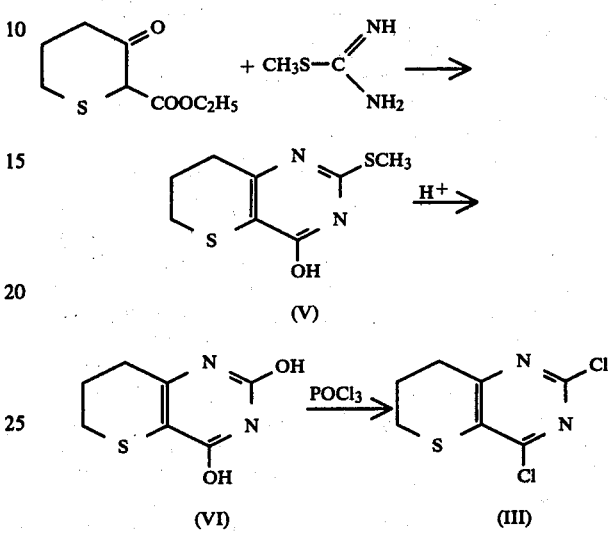

According to the above reaction scheme, ethyl 3-oxotetrahydrothiopyran-2-carboxylate is reacted with S-methylisothiourea in the presence of a basic catalyst such as potassium hydroxide, sodium hydroxide, potassium carbonate, sodium carbonate, sodium hydride, sodium methoxide, sodium ethoxide and the like, in a solvent such as methanol, ethanol, isopropyl alcohol, N,N-dimethylformamide to produce a 2-methylthio-thiopyranopyrimidine compound (V), and the resulting compound (V) is then heated under acidic conditions, preferably in a mixture of acetic acid and water to produce a 2,4-dihydroxythiopyranopyrimidine compound (VI). Subsequently, the resulting 2,4-dihydroxy compound (VI) is reacted with phosphorus oxychloride in the absence or presence of a tertiary amine such as N,N-dimethylaniline, N,N-diethylaniline and the like to obtain the starting material of the formula (III).

The compound of the formula (I) thus-obtained is a free base and can be easily converted into a mono-acid or di-acid addition salt thereof by a conventional procedure, for example, by reacting the base with any desirable non-toxic acid in a solvent such as water, methanol, ethanol, isopropyl alcohol, dichloromethane, chloroform and the like.

The compounds of the present invention can be administered to mammals including human orally or parenterally, e.g., intravenously, alone or in admixture with other pharmaceutical carriers, excipient, binders, lubricant and the like, in dosage forms such as tablets, granules, powders, capsules, injectable preparations and the like. Examples of suitable carriers, excipients, binders, lubricants, etc., for formulating into the above dosage forms include starch, dextrin, sucrose, lactose, silicic acid, carboxymethyl cellulose, cellulose, gelatin, polyvinyl pyrrolidone, glycerin, agar, calcium carbonate, sodium bicarbonate, paraffin, cetyl alcohol, stearic acid ester, kaolin, bentonite, talc, calcium stearate, magnesium stearate, polyethylene glycol, water, ethanol, isopropyl alcohol, propylene glycol and the like.

The dosage level of the compounds of the formula (I) and the pharmaceutically acceptable acid addition salts thereof is usually in the range of from about 0.1 to 20 mg/kg of body weight per day by oral administration and from 0.01 to 3 mg/kg of body weight per day by intravenous injection per day, either in a single dose or multiple doses, but the dosage level can, of course, be reduced or increased appropriately depending upon the severity of conditions to be treated, the sage of patients and other various factors.

The present invention is further illustrated in greater detail by the following Examples, but is not limited to these Examples.

EXAMPLE 1

11 g of 2-amino-4-chloro-7,8-dihydro-6H-thiopyrano[3,2-d]pyrimidine was dissolved in 150 ml of benzene and 30 g of anhydrous piperazine was added thereto while hot. After heating for 3 hours, the mixture was concentrated under reduced pressure and water was added thereto. The mixture was rendered alkaline with potassium carbonate and extracted with chloroform. The organic layer was dried over magnesium sulfate and the solvent was distilled off to obtain crystals. The resulting crystals were converted into the corresponding hydrochloride in methanol and, after treatment with activated carbon, the hydrochloride was again converted into a free base form. The free base was recrystallized from a mixture of chloroform and diethyl ether to obtain 11 g of 2-amino-4-piperazino-7,8-dihydro-6H-thiopyrano[3,2-d]pyrimidine as colorless needles having a melting point of 176°–178° C.

NMR (CDCl$_3$) δ: 1.80 (1H, br s), 1.96–2.40 (2H, m), 2.60–3.15 (8H, m), 3.22–3.53 (4H, m), 4.99 (2H, br s).

A portion of the free base thus-obtained was converted into the maleate in ethanol and recrystallized from methanol-water-isopropyl alcohol to obtain 2-amino-4-piperazino-7,8-dihydro-6H-thiopyrano[3,2-d]pyrimidine dimaleate having a melting point of 185°–187° C.

Dihydrochloride: Recrystallized from methanol-isopropyl alcohol. Colorless needles. Melting point: 231°–234° C.

The starting material, 2-amino-4-chloro-7,8-dihydro-6H-thiopyrano[3,2-d]pyrimidine, was prepared in the following manner. 56.4 g of ethyl 3-oxotetrahydrothiopyran-2-carboxylate was added to a solution of 6.9 g of sodium metal in 300 ml of ethanol at room temperature while stirring. After stirring overnight, water was added to the mixture, and the mixture was rendered acidic with acetic acid. The precipitated crystals were filtered, washed with water and then with a small amount of isopropyl alcohol and air-dried to obtain 45 g of 2-amino-4-hydroxy-7,8-dihydro-6H-thiopyrano[3,2-d]pyrimidine as colorless needles having a melting point above 300° C.

NMR (CDCl$_3$) δ: 1.70–2.25 (2H, m), 2.30–2.66 (2H, m), 2.69–3.03 (2H, m), 6.10–6.83 (2H, m).

14 g of the above product, 65 ml of phosphorus oxychloride and 10 ml of N,N-dimethylaniline were heated at a bath temperature of 135° C. for 1 hour and, after cooling, the reaction mixture was decomposed by pouring on ice. The mixture was adjusted to a pH of about 4 wth aqueous ammonia, and the precipitated crystals were separated by filtration, washed with water and then with a small amount of diethyl ether, and air-dired to obtain 14 g of brown crystals. A portion of the crystals thus-obtained was recrystallized from chloroform to obtain 2-amino-4-chloro-7,8-dihydro-6H-thiopyrano[3,2-d]pyrimidine as colorless prisms having a melting point of 196°–198° C.

NMR (CDCl$_3$) δ: 1.95–2.50 (2H, m), 2.60–3.30 (4H, m), 5.32 (2H, br s).

EXAMPLE 2

In the same manner as described in Example 1, 2-amino-4-(N-methylpiperazino)-7,8-dihydro-6H-thiopyrano-[3,2-d]pyrimidine was prepared, which was recrystallized from dichloromethane-diethyl ether. Colorless prisms. Melting point: 156°–159° C.

NMR (CDCl$_3$) δ: 1.90–3.05 (10H, m), 2.33 (3H, s), 3.20–3.70 (4H, m), 5.10 (2H, br s).

Dimaleate: Recrystallized from methanol-water. Colorless prisms. Melting point: 180°–185° C. (with decomposition).

EXAMPLE 3

3 g of 2-amino-4-piperazino-7,8-dihydro-6H-thiopyrano[3,2-d]pyrimidine obtained as described in Example 1 was dissolved in 50 ml of N,N-dimethylformamide, and the solution was heated in the presence of 7 g of potassium carbonate with stirring. 5 g of benzyl chloride was then added dropwise thereto and the mixture was allowed to react for 3 hours. After cooling, diethyl ether and water were added to the mixture, which was then rendered acidic with hydrochloric acid. The aqueous layer was separated, rendered alkaline with potassium carbonate and extracted with chloroform. The organic layer was washed with water, dried over magnesium sulfate, and the solvent was distilled off. The crude crystals thus-obtained were recrystallized from benzenediethyl ether to obtain 3 g of 2-amino-4-(N-benzylpiperazino)-7,8-dihydro-6H-thiopyrano[3,2-d]pyrimidine as colorless flakes having a melting point of 124°–127° C.

NMR (CDCl$_3$) δ: 2.03–2.46 (2H, m), 2.47–3.06 (8H, m), 3.30–3.65 (4H, m), 3.56 (2H, s), 4.81 (2H, br s), 7.16–7.50 (5H, m).

Dihydrochloride: Recrystallized from methanol-isopropyl alcohol. Colorless prisms. Melting point: 215°–217° C.

EXAMPLE 4

7 g of 2-chloro-4-(N-formylpiperazino)-7,8-dihydro-6H-thiopyrano[3,2-d]pyrimidine was dissolved in 100 ml of a mixture of methanol-ethanol (1:1 by volume), and 50 ml of a 40% aqueous solution of methylamine was added thereto, followed by gently stirring while warming for 7 hours. A large amount of water was added to the mixture which was then extracted with chloroform. The organic layer was washed with water and dried over magnesium sulfate. The solvent was distilled off and the resulting residue was purified by silica gel column chromatography (eluted with ethyl acetate-n-hexane, 1:1 by volume) to obtain 3 g of 2-methylamino-4-(N-formylpiperazino)-7,8-dihydro-6H-thiopyrano[3,2-d]pyrimidine as colorless prisms having a melting point of 149°–151° C.

NMR (CDCl$_3$) δ: 1.95–2.43 (2H, m), 2.63–3.08 (4H, m), 2.96 (3H, m), 3.25–3.85 (8H, m), 4.97 (1H, m), 8.10 (1H, s).

The starting material, 2-chloro-4-(N-formylpiperazino)-7,8-dihydro-6H-thiopyrano[3,2-d]pyrimidine, was prepared in the following manner. 40 g of 2,4-dichloro-7,8-dihydro-6H-thiopyrano[3,2-d]pyrimidine was dissolved in 200 ml of chloroform and 87 g of N-formylpiperazine was added dropwise to the solution under ice-cooling, followed by stirring for 2 hours. Water was then added to the mixture, and the chloroform layer was separated, washed with water and dried over magnesium sulfate. The solvent was then distilled off and the product was recrystallized from dichloromethane-petroleum ether to obtain 40 g of the desired product. Melting point: 138°–140° C.

NMR (CDCl$_3$) δ: 2.05–2.53 (2H, m), 2.76–3.20 (4H, m), 3.36–3.86 (8H, m), 8.12 (1H, s).

EXAMPLE 5

2.5 g of 2-methylamino-4-(N-formylpiperazino)-7,8-dihydro-6H-thiopyrano[3,2-d]pyrimidine obtained in Example 4, 50 ml of ethanol and 4 ml of concentrated hydrochloric acid were heated on a water bath for 2 hours. After cooling, water was added thereto, and the mixture was rendered alkaline with potassium carbonate and extracted with chloroform. The chloroform layer was washed with water and dried over magnesium sulfate. The solvent was distilled off and the residue was converted into the corresponding maleate in 50 ml of ethanol. The maleate was recrystallized from methanol-isopropyl alcohol to obtain 2.5 g of 2-methylamino-4-piperazino-7,8-dihydro-6H-thiopyrano[3,2-d]pyrimidine dimaleate as colorless needles having a melting point of 162°–165° C.

EXAMPLE 6

In the same manner as described in Example 4, 2-morpholino-4-(N-formylpiperazino)-7,8-dihydro-6H-thiopyrano[3,2-d]pyrimidine was prepared, which was then recrystallized from dichloromethane-petroleum ether. Colorless needles. Melting point: 131°–134° C.

NMR (CDCl$_3$) δ: 1.90–2.40 (2H, m), 2.52–3.06 (4H, m), 3.23–3.90 (16H, m), 8.06 (1H, s).

EXAMPLE 7

2.3 g of 2-morpholino-4-(N-formylpiperazino)-7,8-dihydro-6H-thiopyrano[3,2-d]pyrimidine obtained as described in Example 6, 10 ml of ethanol and 3 ml of concentrated hydrochloric acid were heated on a water bath for 30 minutes and, after cooling, water was added thereto. The mixture was rendered alkaline with potassium carbonate and extracted with chloroform. The extract was dried over magnesium sulfate and the solvent was distilled off to obtain 2 g of 2-morpholino-4-piperazino-7,8-dihydro-6H-thiopyrano[3,2-d]pyrimidine as a yellow oil.

NMR (CDCl$_3$) δ: 1.86 (1H, s), 2.00–2.45 (2H, m), 2.63–3.18 (8H, m), 3.23–3.56 (4H, m), 3.72 (8H, s).

Maleate: Recrystallized from methanol-water. Colorless needles. Melting point: 202°–204° C.

EXAMPLE 8

In the same manner as described in Example 4, 2-piperidino-4-(N-formylpiperazino)-7,8-dihydro-6H-thiopyrano[3,2-d]pyrimidine was prepared, which was recrystallized from dichloromethane-petroleum ether. Colorless needles. Melting point: 103°–105° C.

NMR (CDCl$_3$) δ: 1.40–1.83 (6H, m), 2.00–2.46 (2H, m), 2.60–3.13 (4H, m), 3.20–3.90 (12H, m), 8.06 (1H, s).

EXAMPLE 9

In the same manner as described in Example 7, 2-piperidino-4-piperazino-7,8-dihydro-6H-thiopyrano[3,2-d]pyrimidine was obtained from 2-piperidino-4-(N-formylpiperazino)-7,8-dihydro-6H-thiopyrano[3,2-d]pyrimidine obtained in Example 8. Colorless oil.

NMR (CDCl$_3$) δ: 1.46–1.80 (6H, m), 1.86 (1H, s), 2.03–2.46 (2H, m), 2.63–3.16 (8H, m), 3.23–3.53 (4H, m), 3.53–3.90 (4H, m).

Dimaleate: Recrystallized from methanol-water-isopropyl alcohol. Colorless needles. Melting point: 198°–200° C.

EXAMPLE 10

In the same manner as described in Example 4, 2-dimethylamino-4-(N-formylpiperazino)-7,8-dihydro-6H-thiopyrano[3,2-d]pyrimidine was prepared. Recrystallized from dichloromethane-petroleum ether. Colorless prisms. Melting point: 132°–133° C.

NMR (CDCl$_3$) δ: 1.95–2.47 (2H, m), 2.62–3.05 (4H, m), 3.09 (6H, s), 3.23–3.85 (8H, m), 8.08 (1H, s).

EXAMPLE 11

In the same manner as described in Example 7, 2-dimethylamino-4-piperazino-7,8-dihydro-6H-thiopyrano[3,2-d]pyrimidine was prepared from 2-dimethylamino-4-(N-formylpiperazino)-7,8-dihydro-6H-thiopyrano[3,2-d]pyrimidine obtained in Example 10. Recrystallized from dichloromethane-petroleum ether. Colorless prisms.

NMR (CDCl$_3$) δ: 1.92 (1H, s), 1.97–2.43 (2H, m), 2.62–3.20 (8H, m), 3.09 (6H, s), 3.25–3.65 (4H, m).

The resulting free base was converted into the corresponding fumarate. Recrystallized from ethanol-water. Colorless prisms. Melting point: 155°–157° C.

EXAMPLE 12

In the same manner as described in Example 4, 2-pyrrolidino-4-(N-formylpiperazino)-7,8-dihydro-6H-thiopyrano[3,2-d]pyrimidine was prepared. Recrystallized from ethyl acetate-n-hexane. Colorless prisms. Melting point: 135°–137° C.

NMR (CDCl$_3$) δ: 1.79–2.43 (6H, m), 2.63–3.07 (4H, m), 3.27–3.83 (12H, m), 8.08 (1H, s).

EXAMPLE 13

In the same manner as described in Example 7, 2-pyrrolidino-4-piperazino-7,8-dihydro-6H-thiopyrano[3,2-d]pyrimidine was prepared from 2-pyrrolidino-4-(N-formylpiperazino)-7,8-dihydro-6H-thiopyrano[3,2-d]pyrimidine obtained in Example 12. Recrystallized from benzene-petroleum ether. Colorless prisms. Melting point: 130°–132° C.

NMR (CDCl$_3$) δ: 1.77–2.40 (7H, m), 2.60–3.13 (8H, m), 3.20–3.75 (8H, m).

Dimaleate: Recrystallized from ethanol-water. Colorless prisms. Melting point: 166°–169° C.

EXAMPLE 14

In the same manner as described in Example 3, 4-(N-benzylpiperazino)-2-pyrrolidino-7,8-dihydro-6H-thiopyrano[3,2-d]pyrimidine was prepared from 2-pyrrolidino-4-piperazino-7,8-dihydro-6H-thiopyrano[3,2-d]pyrimidine obtained in Example 13. Colorless flakes. Melting point: 137°–139° C.

NMR (CDCl$_3$) δ: 1.80–2.42 (6H, m), 2.45–3.02 (8H, m), 3.30–3.70 (10H, m), 7.18–7.50 (5H, m).

Dichloride: Recrystallized from acetone-methanol. Pale yellow prisms. Melting point: 193°–195° C.

EXAMPLE 15

4 g of 2-chloro-4-(N-methylpiperazino)-7,8-dihydro-6H-thiopyrano[3,2-d]pyrimidine was dissolved in 50 ml of ethanol and the resulting solution was heated with 30 ml of an aqueous solution of dimethylamine in a sealed tube at a temperature of 90° to 100° C. for 5 hours. The mixture was concentrated and extracted with chloroform. The extract was washed with water and dried over magnesium sulfate. The solvent was distilled off and the resulting oily substance was converted into the maleate in ethanol-diethyl ether. The maleate was recrystallized from ethanol-isopropyl alcohol to obtain 6 g of 2-dimethylamino-4-(N-methylpiperazino)-7,8-dihydro-6H-thiopyrano[3,2-d]pyrimidine dimaleate as colorless prisms having a melting point of 143°-144° C. A portion of the dimaleate was rendered alkaline with potassium carbonate and extracted with dichloromethane to obtain the free base as a yellow oil.

NMR (CDCl$_3$) δ: 1.95-3.05 (10H, m), 2.32 (3H, s), 3.12 (6H, s), 3.30-3.70 (4H, m).

The starting material, 2-chloro-4-(N-methylpiperazino)-7,8-dihydro-6H-thiopyrano[3,2-d]pyrimidine, was prepared from 2,4-dichloro-7,8-dihydro-6H-thiopyrano[3,2-d]pyrimidine and N-methylpiperazine according to the procedure as described in Example 4. Colorless prisms. Melting point: 81°-84° C.

NMR (CDCl$_3$) δ: 2.00-2.70 (6H, m), 2.37 (3H, s), 2.73-3.16 (6H, m), 2.34-3.80 (4H, m).

EXAMPLE 16

In the same manner as described in Example 15, 4-(N-methylpiperazino)-2-morpholino-7,8-dihydro-6H-thiopyrano[3,2-d]pyrimidine was prepared. Recrystallized from diethyl ether-petroleum ether. Colorless needles. Melting point: 114°-115° C.

NMR (CDCl$_3$) δ: 1.95-3.06 (10H, m), 2.35 (3H, s), 3.33-3.60 (4H, m), 3.70 (8H, br s).

Dimaleate: Recrystallized from methanol-isopropyl alcohol. Colorless needles. Melting point: 150°-151° C.

EXAMPLE 17

12 g of anhydrous piperazine was dissolved in 70 ml of benzene and 5 g of 4-amino-2-chloro-7,8-dihydro-6H-thiopyrano[3,2-d]pyrimidine was added to the solution while hot. After heating the mixture for 3 hours, the mixture was concentrated under reduced pressure, rendered alkaline with potassium carbonate and extracted with chloroform. The extract was washed with 10% hydrochloric acid, and the aqueous layer was rendered alkaline and extracted with chloroform. The extract was dried over magnesium sulfate and the solvent was distilled off. The residue was converted into the maleate in ethanol and recrystallized from methanol-isopropyl alcohol to obtain 4 g of 4-amino-2 piperazino-7,8-dihydro-6H-thiopyrano[3,2-d]pyrimidine monomaleate as colorless needles having a melting point of 163°-165° C. A portion of the resulting maleate was converted into the free base and recrystallized from dichloromethane-petroleum ether to obtain colorless prisms having a melting point of 110°-112° C.

NMR (CDCl$_3$) δ: 1.90-2.43 (3H, m), 2.56-3.16 (8H, m), 3.55-3.87 (4H, m), 4.93 (2H, br s).

The starting material, 4-amino-2-chloro-7,8-dihydro-6H-thiopyrano[3,2-d]pyrimidine, was prepared by heating 2,4-dichloro-7,8-dihydro-6H-thiopyrano[3,2-d]pyrimidine, aqueous ammonia and ethanol in a sealed tube at a bath temperature of about 100° C. for several hours and recrystallizing the resulting product from ethanol. Melting point: 196°-197° C.

EXAMPLE 18

In the same manner as described in Example 17, 4-amino-2-(N-methylpiperazino)-7,8-dihydro-6H-thiopyrano[3,2-d]pyrimidine was obtained, which was then recrystallized from dichloromethane-petroleum ether. Colorless needles. Melting point: 140°-141° C.

NMR (CDCl$_3$) δ: 1.90-3.10 (10H, m), 2.28 (3H, s), 3.47-3.83 (4H, m), 4.98 (2H, br s).

Dimaleate: Recrystallized from methanol. Colorless needles. Melting point: 168°-170° C.

EXAMPLE 19

In the same manner as described in Example 17, 4-methylamino-2-piperazino-7,8-dihydro-6H-thiopyrano[3,2-d]pyrimidine was prepared from 2-chloro-4-methylamino-7,8-dihydro-6H-thiopyrano[3,2-d]pyrimidine and anhydrous piperazine. Recrystallized from benzene-petroleum ether. Colorless needles. Melting point: 105°-107° C.

NMR (CDCl$_3$) δ: 1.88 (1H, s), 1.95-2.40 (2H, m), 2.50-3.06 (8H, m), 2.95 (3H, d), 3.60-3.80 (4H, m), 4.68 (1H, m).

Dimaleate: Recrystallized from methanol-isopropyl alcohol. Colorless needles. Melting point: 172°-174° C.

The starting material, 2-chloro-4-methylamino-7,8-dihydro-6H-thiopyrano[3,2-d]pyrimidine, was prepared by heating 2,4-dichloro-7,8-dihydro-6H-thiopyrano[3,2-d]pyrimidine, an aqueous solution of methylamine and tetrahydrofuran in a sealed tube at a bath temperature of about 100° C. for several hours, treating the reaction mixture in a usual manner and recrystallizing the resulting product from ethanol. Melting point: 171°-172° C.

NMR (CDCl$_3$) δ: 1.93-2.47 (2H, m), 2.53-3.20 (7H, m), 4.67-5.07 (1H, m).

EXAMPLE 20

In the same manner as described in Example 18, 4-methylamino-2-(N-methylpiperazino)-7,8-dihydro-6H-thiopyrano[3,2-d]pyrimidine was prepared, which was then recrystallized from dichloromethane-n-hexane. Colorless needles. Melting point: 171°-173° C.

NMR (CDCl$_3$) δ: 2.00-3.17 (13H, m), 2.33 (3H, s), 3.67-3.97 (4H, m), 4.43-4.83 (1H, m).

EXAMPLE 21

In the same manner as described in Example 3, 2-[N-(o-chlorobenzyl)piperazino]-4-methylamino-7,8-dihydro-6H-thiopyrano[3,2-d]pyrimidine was prepared from 4-methylamino-2-piperazino-7,8-dihydro-6H-thiopyrano[3,2-d]pyrimidine and o-chlorobenzyl chloride. Recrystallized from dichloromethane-diethyl ether. Colorless needles. Melting point: 82°-85° C.

NMR (CDCl$_3$) δ: 1.95-2.36 (2H, m), 2.42-3.08 (8H, m), 2.93 (3H, d), 3.60-3.95 (4H, m), 3.64 (2H, s), 4.60 (1H, m), 7.07-7.65 (4H, m).

Dihydrochloride: Recrystallized from methanol-acetone. Colorless needles. Melting point: 195°-198° C.

EXAMPLE 22

10 g of 2-chloro-4-pyrrolidino-7,8-dihydro-6H-thiopyrano[3,2-d]pyrimidine, 10 g of piperazine and 50 ml of benzene were heated at a bath temperature of 70°-80° C. for 4 hours. The solvent was then distilled off and the resulting residue was dissolved in dichloromethane. The solution was washed with water and dried. The solvent was distilled off and the resulting crystals were washed thoroughly with diethyl ether to obtain 7.3 g (61% yield) of 2-piperazino-4-pyrrolidino-7,8-dihydro-6H-thiopyrano[3,2-d]pyrimidine.

NMR (CDCl$_3$) δ: 1.57–2.30 (6H, m), 1.83 (1H, s), 2.40–2.97 (8H, m), 3.37–3.83 (8H, m).

The crystals thus-obtained were then reacted with a slightly excess amount of maleic acid while hot and the resulting crystals were recrystallized from a mixture of ethanol-diethyl ether to obtain 2-piperazino-4-pyrrolidino-7,8-dihydro-6H-thiopyrano[3,2-d]pyrimidine maleate as colorless needles having a melting point of 183° C.

The starting material, 2-chloro-4-pyrrolidino-7,8-dihydro-6H-thiopyrano[3,2-d]pyrimidine, was prepared in the following manner.

20 g of ethyl 3-oxotetrahydrothiopyran-2-carboxylate was added to 120 ml of a methanolic solution containing 9 g of potassium hydroxide at room temperature while stirring. Then, a small amount of S-methylisothiourea hydrobromide was added to the mixture and the stirring was continued for 2 hours. The reaction solution was then poured into ice-water, and the mixture was made acidic with acetic acid. The precipitated crystals were separated by filtration and recrystallized from acetic acid to obtain 4-hydroxy-2-methylthio-7,8-dihydro-6H-thiopyrano[3,2-d]pyrimidine as colorless needles having a melting point of 248° C.

NMR (DMSO-d$_6$) δ: 1.90–3.10 (6H, m), 2.50 (3H, m).

24 g of the crystals thus-obtained was added to a mixture of 120 ml of acetic acid and 70 ml of water, and the mixture was refluxed for 50 hours. After cooling, the precipitated crystals were separated by filtration and recrystallized from N,N-dimethylformamide to obtain 19 g (92% yield) of 2,4-dihydroxy-7,8-dihydro-6H-thiopyrano[3,2-d]pyrimidine having a melting point above 300° C.

NMR (DMSO-d$_6$) δ: 1.80–2.23 (2H, m), 2.30–2.67 (2H, m), 2.70–3.00 (2H, m), 10.84 (1H, br s), 11.50 (1H, br s).

Then, a mixture of 6 g of the crystals thus-obtained, 15 ml of phosphorus oxychloride and 1 ml of N,N-dimethylaniline was refluxed for 3 hours. After cooling, the reaction solution was poured into ice-water, and the mixture was extracted with dichloromethane. The extract was washed with water and dried. The solvent was distilled off and the resulting crystals were recrystallized from dichloromethane-n-hexane to obtain 6 g (83% yield) of 2,4-dichloro-7,8-dihydro-6H-thiopyrano[3,2-d]pyrimidine as colorless prisms having a melting point of 110° C.

NMR (CDCl$_3$) δ: 2.07–2.60 (2H, m), 2.78–3.37 (4H, m).

20 g of the crystals thus-obtained was dissolved in 80 ml of dichloromethane, and 20 ml of pyrrolidine was added dropwise thereto while cooling with ice-water, followed by stirring for 3 hours. The reaction solution was washed with water, dried and the solvent was distilled off. The resulting residue was recrystallized from ethyl acetate to obtain 17 g (24% yield) of 2-chloro-4-pyrrolidino-7,8-dihydro-6H-thiopyrano[3,2-d]pyrimidine as colorless prisms having a melting point of 76° C.

NMR (CDCl$_3$) δ: 1.50–2.43 (6H, m), 2.50–3.10 (4H, m), 3.53–4.03 (4H, m).

EXAMPLE 23

A mixture of 10 g of 2-chloro-4-pyrrolidino-7,8-dihydro-6H-thiopyrano[3,2-d]pyrimidine and 25 ml of N-methylpiperazine was heated at a bath temperature of 70° to 80° C. for 5 hours. After cooling, 70 ml of chloroform and then water were added to the reaction solution, and the chloroform layer was separated and dried. The solvent was distilled off and the residue was purified by alumina column chromatography (eluted with ethyl acetate) to obtain 9 g (72% yield) of a pale yellow oily substance.

Then, the resulting oily substance was dissolved in ethanol and a slightly excess amount of maleic acid was added thereto to allow the mixture to react while hot. The resulting crystals were recrystallized from a mixture of ethanol-diethyl ether to obtain 2-(N-methylpiperazino)-4-pyrrolidino-7,8-dihydro-6H-thiopyrano[3,2-d]pyrimidine maleate as colorless needles having a melting point of 191° C.

EXAMPLE 24

In the same manner as described in Example 22, 11 g (93% yield) of 4-morpholino-2-piperazino-7,8-dihydro-6H-thiopyrano[3,2-d]pyrimidine was obtained from 10 g of 2-chloro-4-morpholino-7,8-dihydro-6H-thiopyrano[3,2-d]pyrimidine and 30 g of piperazine. Pale yellow crystalline powder.

NMR (CDCl$_3$) δ: 1.80 (1H, s), 1.93–2.33 (2H, m), 2.53–3.02 (8H, m), 3.17–3.50 (4H, m), 3.52–3.87 (8H, m).

Then, the crystalline powder thus-obtained was reacted with maleic acid in ethanol and the resulting crystals were recrystallized from a mixture of ethanol-diethyl ether to obtain 4-morpholino-2-piperazino-7,8-dihydro-6H-thiopyrano[3,2-d]pyrimidine maleate as colorless needles having a melting point of 161° C.

The starting material, 2-chloro-4-morpholino-7,8-dihydro-6H-thiopyrano[3,2-d]pyrimidine, was prepared in the same manner as described in Example 22 by reacting 6.5 g of 2,4-dichloro-7,8-dihydro-6H-thiopyrano[3,2-d]pyrimidine with 20 ml of morpholine and recrystallizing the resulting crystals from a mixture of dichloromethane-n-hexane. Colorless prisms. Melting point: 91° C.

NMR (CDCl$_3$) δ: 1.90–2.40 (2H, m), 2.60–3.10 (4H, m), 3.27–3.93 (8H, m).

EXAMPLE 25

A mixture of 6.5 g of 2-chloro-4-morpholino-7,8-dihydro-6H-thiopyrano[3,2-d]pyrimidine and 15 ml of N-methylpiperazine was heated at a bath temperature of 70° to 80° C. for 3 hours. After cooling, the reaction solution was extracted with chloroform, and the extract was washed with water and dried. The solvent was distilled off and the resulting crystals were recrystallized from a mixture of dichloromethane-n-hexane to obtain 5.5 g (69% yield) of 2-(N-methylpiperazino)-4-morpholino-7,8-dihydro-6H-thiopyrano[3,2-d]pyrimidine as colorless needles having a melting point of 100° C.

NMR (CDCl$_3$) δ: 2.00–2.60 (6H, m), 2.30 (3H, s), 2.62–3.03 (4H, m), 3.27–3.57 (4H, m), 3.63–3.97 (8H, m).

The crystals thus-obtained were then reacted with maleic acid in ethanol and the resulting crystals were recrystallized from a mixture of ethanol-diethyl ether to obtain 2-(N-methylpiperazino)-4-morpholino-7,8-dihydro-6H-thiopyrano[3,2-d]pyrimidine dimaleate as colorless prisms having a melting point of 169° C.

EXAMPLE 26

1.6 g of benzyl chloride was added dropwise to a mixture of 3 g of 4-morpholino-2-piperazino-7,8-dihydro-6H-thiopyrano[3,2-d]pyrimidine, 4 g of potassium carbonate and 30 ml of N,N-dimethylformamide at room temperature under stirring, followed by stirring for 5 hours. The reaction solution was extracted with ethyl acetate, and the extract was washed with water and dried. The solvent was then distilled off and the resulting crystals were recrystallized from a mixture of diethyl ether-petroleum ether to obtain 3.1 g (82% yield) of 2-(N-benzylpiperazino)-4-morpholino-7,8-dihydro-6H-thiopyrano[3,2-d]pyrimidine as pale yellow prisms having a melting point of 125° C.

NMR (CDCl₃) δ: 1.82-3.03 (10H, m), 3.08-3.93 (12H, m), 3.47 (2H, s), 6.95-7.40 (5H, m).

Then, the crystals thus-obtained were reacted with maleic acid in ethanol and the resulting crystals were recrystallized from a mixture of ethanol-diethyl ether to obtain 2-(N-benzylpiperazino)-4-morpholino-7,8-dihydro-6H-thiopyrano[3,2-d]pyrimidine maleate as colorless needles having a melting point of 197° C.

EXAMPLE 27

2-Dimethylamino-4-piperazino-7,8-dihydro-6H-thiopyrano[3,2-d]pyrimidine obtained in Example 11 was reacted with benzyl bromide in the same manner as described in Example 3 to obtain 4-(N-benzylpiperazino)-2-dimethylamino-7,8-dihydro-6H-thiopyrano[3,2-d]pyrimidine which was then recrystallized from dichloromethane-diethyl ether. Colorless prisms. Melting point: 106° to 108° C.

NMR (CDCl₃) δ: 1.95-2.40 (2H, m), 2.45-3.02 (8H, m), 3.09 (6H, s), 3.33-3.65 (4H, m), 3.54 (2H, s), 7.13-7.45 (5H, m).

Dihydrochloride: Recrystallized from methanol-acetone. Colorless prisms. Melting point: 199°-205° C.

EXAMPLE 28

In the same manner as described in Example 20, 6 g of 2-chloro-4-(2-hydroxyethyl)amino-7,8-dihydro-6H-thiopyrano[3,2-d]pyrimidine was reacted with 15 g of N-methylpiperazine to obtain 7.2 g of 4-(2-hydroxyethyl)amino-2-(N-methylpiperazino)-7,8-dihydro-6H-thiopyrano[3,2-d]pyrimidine which was then recrystallized from methanol-diethyl ether. Colorless prisms. Melting point: 162°-164° C.

NMR (CDCl₃) δ: 1.93-3.20 (10H, m), 2.35 (3H, s), 3.42-3.96 (9H, m), 5.00-5.35 (1H, m).

Dimaleate: Recrystallized from ethanol-water. Colorless prisms. Melting point: 169°-172° C.

The starting material, 2-chloro-4-(2-hydroxyethyl)amino-7,8-dihydro-6H-thiopyrano[3,2-d]pyrimidine, was prepared from 2,4-dichloro-7,8-dihydro-6H-thiopyrano[3,2-d]pyrimidine and ethanolamine in the same manner as described in Example 4. Recrystallized from methanol. Colorless needles. Melting point: 139°-140° C.

EXAMPLE 29

In the same manner as described in Example 17, 2-chloro-4-(2-hydroxyethyl)amino-7,8-dihydro-6H-thiopyrano[3,2-d]pyrimidine was reacted with anhydrous piperazine to obtain 4-(2-hydroxyethyl)amino-2-piperazino-7,8-dihydro-6H-thiopyrano[3,2-d]pyrimidine which was then recrystallized from ethanol. Colorless needles. Melting point: 116°-120° C.

NMR (CDCl₃) δ: 1.95-2.43 (2H, m), 2.56-3.22 (10H, m), 3.43-3.97 (8H, m), 5.00-5.33 (1H, m).

Dimaleate: Recrystallized from methanol-diethyl ether. Colorless needles. Melting point: 169°-171° C.

The pharmacological activities and acute toxicity of typical examples of the compounds (I) of the present invention are described hereinafter in detail in comparison with some prior art compounds. The compounds used in the experimentations are as follows:

Compound A: 4-Amino-2-(N—methylpiperazino)-7,8-dihydro-6H—thiopyrano[3,2-d]pyrimidine Dimaleate (Example 18)
Compound B: 4-Methylamino-2-piperazino-7,8-dihydro-6H—thiopyrano[3,2-d]pyrimidine Dimaleate (Example 19)
Compound C: 2-Amino-4-piperazino-7,8-dihydro-6H—thiopyrano[3,2-d]pyrimidine Dimaleate (Example 1)
Compound D: 4-Amino-2-piperazino-7,8-dihydro-6H—thiopyrano[3,2-d]pyrimidine Dimaleate (Example 17)
Compound E: 2-Piperazino-4-pyrrolidino-7,8-dihydro-6H—thiopyrano[3,2-d]pyrimidine Maleate (Example 22)
Compound F: 2-(N—Methylpiperazino)-4-pyrrolidino-7,8-dihydro-6H—thiopyrano[3,2-d]pyrimidine Maleate (Example 23)
Compound G: 4-Morpholino-2-piperazino-7,8-dihydro-6H—thiopyrano[3,2-d]pyrimidine Maleate (Example 24)
Compound H: 2-(N—Methylpiperazino)-4-morpholino-7,8-dihydro-6H—thiopyrano[3,2-d]pyrimidine Maleate (Example 25)

Hypoglycemic Activity (a) Effect on Alloxan Diabetes Mice

Alloxan was administered intravenously at a dose of 40 mg/kg from a tail vein to ddY male mice weighing 28.2 to 29.5 g. Seven days after administration, the test compound was administered orally to the mice and the blood sugar level was determined before and 2 hours after the administration of the test compound. The results obtained are shown in Table 1 below.

TABLE 1

| Test Compound | Dose (mg/kg, oral) | Number of Mice | Blood Sugar Level mg/dl Mean ± S.E. | % Change in Blood Sugar Level |
|---|---|---|---|---|
| Control | — | 8 | 322.6 ± 30.3 | — |
| Compound E | 200 | 8 | 205.5 ± 29.3** | −36.3 |
| Compound G | 200 | 7 | 195.2 ± 39.7* | −39.5 |
| Buformin (1-Butyl-biguanide) | 150 | 8 | 273.3 ± 28.7 | −15.3 |
| Tolbutamide (1-Butyl-3-(p-tolylsulfonyl)-urea) | 500 | 7 | 278.4 ± 25.7 | −13.7 |

*P < 0.05
**P < 0.01
(Student's t-test)

As is apparent from the results shown in Table 1, Compounds E and G exhibit a significant hypoglycemic activity at a dose of 200 mg/kg. On the other hand, Buformin and Tolbutamide used as controls show weak hypoglycemic activity at a dose of 150 mg/kg and 500 mg/kg, respectively, but the activity is not significant as compared with the activities of the compounds of the present invention.

(b) Effect on Alloxan Diabetes Rats (1) Alloxan was administered intravenously at a dose of 30 mg/kg from a tail vein to Wister male rats weighing 200 to 218 g. Three days after administration, the test compound was administered orally to the rats and the blood sugar level was determined before and 2 hours after administration of the test compound. The results obtained are shown in Table 2 below.

TABLE 2

| Test Compound | Dose (mg/kg, oral) | Number of Rats | Blood Sugar Level mg/dl Mean ± S.E. | % Change in Blood Sugar Level |
|---|---|---|---|---|
| Control | — | 5 | 34.47 ± 13.6 | — |
| Compound G | 100 | 6 | 286.3 ± 76** | −30.2 |
| Buformin | 100 | 6 | 275.5 ± 6.0* | −22.9 |
| Tolbutamide | 300 | 6 | 285.2 ± 2.8** | −18.6 |

*$P < 0.01$
**$P < 0.001$
(Student's t-test)

As shown in Table 2, each of Compound G (at 100 mg/kg), Buformin (at 100 mg/kg) and Tolbutamide (at 300 mg/kg) shows a significant hypoglycemic activity, but Compound G has the strongest activity.

(2) Alloxan was administered intravenously at a dose of 18 mg/kg to 9–10W Wister male rats weighing 240 to 280 g. Three days after administration, the test compound was administered orally to the rats (after fasting for 4 hours) and the blood sugar level was determined before and 1, 2 and 3 hours after administration of the test compound with respect to the blood samples drawn from the jugular vein by the o-toluidine-boric acid method. The results obtained are shown in Table 3 below.

TABLE 3

| Test Compound | Dose (mg/kg, oral) | Blood Sugar Level (mg/kg) Mean ± S.E. | | | |
|---|---|---|---|---|---|
| | | Before | After 1 Hr. | After 2 Hrs. | After 3 Hrs. |
| Control | — | 187.5 ± 9.8 | 207.5 ± 12.1 | 189.2 ± 17.0 | 183.3 ± 24.7 |
| Compound G | 100 | 189.5 ± 9.4 | 141.3 ± 10.4** | 130.6 ± 12.6* | 130.3 ± 10.3* |

*$P < 0.05$
**$P < 0.001$
(Student's t-test)

(c) Effect on Alloxan Diabetes Mice

Alloxan was administered intravenously at a dose of 50 mg/kg from a tail vein to 5W ddY male mice weighing 23 to 27 g (10 rats per group). Seven days after administration, the test compound was administered orally to the mice and a blood sample was collected from the sacrificed mice after 3 hours. The blood sugar level of the sample was determined by the o-toluidine-boric acid method. The percent inhibition was calculated from the values in test group and the control, and a 20% inhibitory effective dose (ED$_{20}$) was determined from a dose response curve. The results obtained are shown in Table 4 below.

(d) Effect on Normal Mice

The test compound was administered orally to 6W ddY male mice and, 3 hours after administration, a blood sample was drawn from the sacrificed mice. The blood sugar level of the sample was determined and ED$_{20}$ values were calculated in the same manner as described in (c) above. The results obtained are also shown in Table 4 below.

TABLE 4

| | ED$_{20}$ Value | |
|---|---|---|
| Test Compound | Alloxan Diabetes Mice (mg/kg, oral) | Normal Mice (mg/kg, oral) |
| Compound A | 60 | 127 |
| Compound B | 53 | 37 |
| Compound C | 47 | 230 |
| Compound D | 52 | 11 |

Effect on Inhibition of Platelet Aggregation

A blood sample drawn from a jugular vein of unanesthetized male rabbits (body weight: 2.2 to 2.6 kg) was mixed with a 3.8% aqueous sodium citrate solution in a proportion of 9:1 (by volume) and the mixture was centrifuged at 1,000 rpm for 10 minutes to obtain a platelet-rich plasma (about $5 \times 10^5$ platelets/mm$^3$, hereinafter "PRP"). To 180 μg of PRP was added 10 μg of an aqueous solution of the test compound and, after 2 hours, to the mixture was added either an adenosine diphosphate (ADP) solution (final concentration: $5 \times 10^{-6}$ M), a sodium arachidonate solution (final concentration: $5 \times 10^{-4}$ M) or collagen. The percent platelet aggregation was determined using an aggregometer and the inhibition of platelet aggregation by the test compound was calculated. The results obtained are shown in Table 5 below.

TABLE 5

| Test Compound | ADP IC$_{50}$ (M) | Arachidonic Acid OC$_{50}$ (M) | Collagen ($5 \times 10^{-4}$ g/ml) Percent Inhibition (%) |
|---|---|---|---|
| F | | $3.0 \times 10^{-5}$ | 73 |
| G | $1.5 \times 10^{-4}$ | $7.5 \times 10^{-4}$ | 95 |
| H | $1.0 \times 10^{-3}$ | $8.4 \times 10^{-6}$ | 65 |
| Acetylsalicylic Acid (Aspirin) | $2.0 \times 10^{-3}$ | $1.8 \times 10^{-4}$ | 46 |

The above results indicate that the compounds of the present invention exhibit strong inhibition to the platelet aggregation by each of the platelet aggregating agents, as compared with Aspirin.

Anti-Histamine Activity

The ileum of Hartley male guinea pig (body weight: 350–400 g) was extracted and suspended in a Magnus tube containing 40 ml of Tyrode solution and the muscle movement was recorded on a soot paper via an isotonic Hebel. The solution in the Magnus tube was maintained at 25±0.5° C. during the test and test compound was previously added to the solution. Histamine was added after 5 minutes and pA$_2$ value was calculated by the cumulative technique method. The results obtained are shown in Table 6 below.

TABLE 6

| Test Compound | pA$_2$ Value |
|---|---|
| Compound E | 7.37 |
| Compound F | 7.69 |
| Diphenhydramine | 7.40 |

The above results indicate that Compounds E and F have an anti-histamine activity to a degree of substantially equal to that of Diphenhydramine.

Acute Toxicity

The test compound was administered orally (p.o.) or intravenously (i.v.) from a tail vein to ddY male mice weighing 24±2 g. The LD$_{50}$ values were calculated by the Behrens-Kärber method [Arch. exp. Path. Pharmak., 177, 379 (1935)] from the mortality one week after administration. The results obtained are shown in Table 7 below.

TABLE 7

| Test Compound | LD$_{50}$ (mg/kg) | |
|---|---|---|
| | i.v. | p. o. |
| A | — | 1,450 |
| B | — | 580 |
| C | — | 1,400 |
| D | — | 820 |
| E | 125 | 1,170 |
| F | 100 | 1,250 |
| G | 135 | 960 |
| H | 200 | 1,580 |

What is claimed is:

1. A thiopyranopyrimidine compound represented by the formula (I)

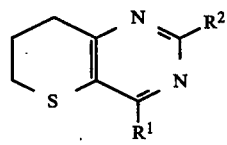

wherein R$^1$ represents an amino group, a methylamino group, a hydroxyethylamino group, a pyrrolidino group, a morpholino group, a piperazino group or an N-substituted piperazino group, and R$^2$ represents an amino group, a methylamino group, a dimethylamino group, a piperazino group, an N-substituted piperazino group, a pyrrolidino group, a piperidino group or a morpholino group, and the pharmaceutically acceptable acid addition salt thereof.

2. 4-Amino-2-(N-methylpiperazino)-7,8-dihydro-6H-thiopyrano[3,2-d]pyrimidine and the pharmaceutically acceptable acid addition salt thereof, according to claim 1.

3. 4-Methylamino-2-piperazino-7,8-dihydro-6H-thiopyrano[3,2-d]pyrimidine and the pharmaceutically acceptable acid addition salt thereof, according to claim 1.

4. 2-Amino-4-piperazino-7,8-dihydro-6H-thiopyrano[3,2-d]pyrimidine and the pharmaceutically acceptable acid addition salt thereof, according to claim 1.

5. 4-Amino-2-piperazino-7,8-dihydro-6H-thiopyrano[3,2-d]pyrimidine and the pharmaceutically acceptable acid addition salt thereof, according to claim 1.

6. 2-Piperazino-4-pyrrolidino-7,8-dihydro-6H-thiopyrano[3,2-d]pyrimidine and the pharmaceutically acceptable acid addition salt thereof, according to claim 1.

7. 2-(N-Methylpiperazino)-4-pyrrolidino-7,8-dihydro-6H-thiopyrano[3,2-d]pyrimidine and the pharmaceutically acceptable acid addition salt thereof, according to claim 1.

8. 4-Morpholino-2-piperazino-7,8-dihydro-6H-thiopyrano[3,2-d]pyrimidine and the pharmaceutically acceptable acid addition salt thereof, according to claim 1.

9. 2-(N-Methylpiperazino)-4-morpholino-7,8-dihydro-6H-thiopyrano[3,2-d]pyrimidine and the pharmaceutically acceptable acid addition salt thereof, according to claim 1.

* * * * *